(12) United States Patent
Yonejima et al.

(10) Patent No.: US 10,287,234 B2
(45) Date of Patent: May 14, 2019

(54) TRIGLYCERIDE AND USE THEREOF

(71) Applicants: NITTO PHARMACEUTICAL INDUSTRIES, LTD., Muko-shi, Kyoto (JP); KYOTO UNIVERSITY, Kyoto-shi, Kyoto (JP)

(72) Inventors: Yasunori Yonejima, Muko (JP); Jun Ogawa, Kyoto (JP); Shigenobu Kishino, Kyoto (JP)

(73) Assignees: NITTO PHARMACEUTICAL INDUSTRIES, LTD., Muko (JP); KYOTO UNIVERSITY, Kyoto (JP)

(*) Notice: Subject to any disclaimer, the term of this patent is extended or adjusted under 35 U.S.C. 154(b) by 0 days.

(21) Appl. No.: 15/578,694

(22) PCT Filed: Jun. 2, 2016

(86) PCT No.: PCT/JP2016/066405
§ 371 (c)(1),
(2) Date: Nov. 30, 2017

(87) PCT Pub. No.: WO2016/195016
PCT Pub. Date: Dec. 8, 2016

(65) Prior Publication Data
US 2018/0170854 A1   Jun. 21, 2018

(30) Foreign Application Priority Data
Jun. 2, 2015 (JP) .................. 2015-112604

(51) Int. Cl.
*C07C 69/732* (2006.01)
*C11C 3/00* (2006.01)
(Continued)

(52) U.S. Cl.
CPC ............ *C07C 69/732* (2013.01); *A23D 9/007* (2013.01); *A23K 20/158* (2016.05); *A23L 33/12* (2016.08);
(Continued)

(58) Field of Classification Search
CPC ................................ C07C 69/732; C11C 3/00
See application file for complete search history.

(56) References Cited

U.S. PATENT DOCUMENTS

2006/0217441 A1   9/2006   Akimoto et al.
2014/0343192 A1   11/2014  Cochran et al.
(Continued)

FOREIGN PATENT DOCUMENTS

JP   H03-074315 A   3/1991
JP   2006-521368 A   9/2006
(Continued)

OTHER PUBLICATIONS

JP 2009-051732, Hiroshi et al., Composition having PPAR ligand activity, English translation, 20 pages (Year: 2009).*
(Continued)

*Primary Examiner* — Yate' K Cutliff
(74) *Attorney, Agent, or Firm* — Leydig, Voit & Mayer, Ltd.

(57) ABSTRACT

The invention provides a HYA derivative having superior physiological functions intrinsic to HYA and permitting easy ingestion and easy handling, and use thereof. In particular, the invention relates to a triglyceride in which at least one fatty acid forming an ester bond with a hydroxy group of glycerol is 10-hydroxy-cis-12-octadecenoic acid, or an optical isomer thereof, and a composition (edible fat or oil, food, medicament, cosmetic etc.) containing same.

24 Claims, 5 Drawing Sheets

(51) Int. Cl.
  *A23D 9/007* (2006.01)
  *A61K 8/37* (2006.01)
  *A61Q 1/00* (2006.01)
  *A61Q 19/00* (2006.01)
  *A61K 31/231* (2006.01)
  *A23K 20/158* (2016.01)
  *A23L 33/12* (2016.01)
  *C07B 53/00* (2006.01)

(52) U.S. Cl.
  CPC .............. *A61K 8/37* (2013.01); *A61K 31/231* (2013.01); *A61Q 1/00* (2013.01); *A61Q 19/00* (2013.01); *C11C 3/00* (2013.01); *C07B 53/00* (2013.01)

(56) References Cited

U.S. PATENT DOCUMENTS

| 2015/0125911 | A1* | 5/2015 | Ogawa | C12R 1/25 435/134 |
| 2015/0342916 | A1 | 12/2015 | Ogawa et al. | |
| 2016/0000739 | A1 | 1/2016 | Ogawa et al. | |

FOREIGN PATENT DOCUMENTS

| JP | 2009-051732 A | 3/2009 |
| WO | WO 2013/168310 A1 | 11/2013 |
| WO | WO 2014/069227 A1 | 5/2014 |
| WO | WO 2014/129384 A1 | 8/2014 |

OTHER PUBLICATIONS

Koritala et al., "Microbial Conversion of Linoleic and Linolenic Acids to Unsaturated Hydroxy Fatty Acids," *Journal of the American Oil Chemists Society*, 69(6): 575-578 (1992).

Miyamoto et al., "A Gut Microbial Metabolite of Linoleic Acid, 10-Hydroxy-cis-12-octadecenoic Acid, Ameliorates Intestinal Epithelial Barrier Impairment Partially via GPR40-MEK-ERK Pathway," *J. Biol. Chem.*, 290(5): 2902-2918 (2015).

Nagao et al., "Conjugated Fatty Acids in Food and Their Health Benefits," *J. Biosci. Bioeng.*, 100(2): 152-157 (2005).

Japanese Patent Office, International Search Report in International Patent Application No. PCT/JP2016/066405 (dated Aug. 9, 2016).

Black et al., "Antifungal Lipids Produced by Lactobacilli and Their Structural Identification by Normal Phase LC/Atmospheric Pressure Photoionization—MS/MS," *J. Agric. Food Chem.*, 61(22): 5338-5346 (2013).

Takeuchi et al., "Hydroxy fatty acid production by *Pediococcus* sp.," *Eur. J. Lipid Sci. Technol.*, 115(4): 386-393 (2013).

Takeuchi et al., "Characterization of hydroxyl fatty acid dehydrogenase involved in polyunsaturated fatty acid saturation metabolism in *Lactobacillus plantarum* AKU 1009a," *Journal of Molecular Catalysis B: Enzymatic*, 117: 7-12 (2015).

European Patent Office, Extended European Search Report in European Patent Application No. 16803450.2 (dated Jan. 16, 2019).

* cited by examiner

TRIGLYCERIDE AND USE THEREOF

CROSS-REFERENCE TO RELATED APPLICATIONS

This patent application is the U.S. national phase of International Patent Application No. PCT/JP2016/066405, filed Jun. 2, 2016, which claims the benefit of Japanese Patent Application No. 2015-112604, filed on Jun. 2, 2015, which are incorporated by reference in their entireties herein.

TECHNICAL FIELD

The present invention relates to a novel triglyceride and a composition containing same, and use thereof, more particularly, triglyceride wherein at least one fatty acid forming an ester bond with a hydroxy group of glycerol is 10-hydroxy-cis-12-octadecenoic acid (hereinafter sometimes to be abbreviated as "HYA") or an optical isomer thereof.

The present invention also relates to a use of the triglyceride or an optical isomer thereof as edible fat or oil, and a composition (food, medicament, cosmetic, feed etc.) containing the triglyceride or an optical isomer thereof.

BACKGROUND ART

In recent years, the physiological function of scarce fatty acid present only at a low ratio in the body has been attracting attention. For example, it has been reported that conjugated fatty acids such as conjugated linoleic acid and the like (non-patent document 1) and ω3 polyvalent unsaturated fatty acids such as eicosapentaenoic acid, docosahexaenoic acid and the like (patent document 1) have lipid metabolism improving effects, diabetes improving effects and the like. There is a high interest in ingesting the aforementioned functional lipids from the diet, and products (foods, etc.) containing them are on the market.

One of the scarce fatty acids is a hydroxylated fatty acid having a hydroxy group in the compound. The physiological functions thereof have not been analyzed sufficiently heretofore due to the absence of a suitable source of supply. Recently, however, a means for highly efficient and highly selective production by an enzymatic reaction using linoleic acid or the like, which is contained in a large amount in vegetable oil, as a starting material has been found (patent document 2). A method of supplying various hydroxylated fatty acids has been secured, along with which studies on the physiological functions thereof have been actively conducted. The present inventors particularly took note of 10-hydroxy-cis-12-octadecenoic acid (HYA) among hydroxylated fatty acids, and reported that HYA has a lipid metabolism abnormality improving effect (patent document 3), an action to enhance intestinal immunity (patent document 4), a suppressive action on intestinal inflammations (non-patent document 2) and the like.

Since it has become easy to obtain high purity HYA as described above, if HYA can be ingested easily, effective utilization of HYA is expected to be promoted by utilizing its physiological functions. However, since the melting point of HYA is about 25° C. ("about" here means±1° C.) and HYA is solid (or partially melted state) at ambient temperature, there was a problem that it is inferior to liquid components in the ease of ingestion and handleability in adding to or mixing with other liquid or solid food components. In addition, the acrid flavor of HYA is an obstacle in ingestion.

On the other hand, a HYA derivative capable of solving the above-mentioned problems has not been reported heretofore.

DOCUMENT LIST

Patent Documents

Patent document 1: National Publication of International Patent Application No. 2006-521368
Patent document 2: WO 2013/168310
Patent document 3: WO 2014/069227
Patent document 4: WO 2014/129384

Non-Patent Documents

Non-patent document 1: Nagao, K., J. Biosci. Bioeng., 2005, vol. 100, no. 2, p. 152-157
Non-patent document 2: Miyamoto, J. et al., J. Biol. Chem., 2015, 290(5), 2902-2918

SUMMARY OF THE INVENTION

Problems to be Solved by the Invention

The problem of the present invention is to provide a novel HYA derivative having superior physiological functions of HYA and permitting easy ingestion and easy handling.

Means of Solving the Problems

The present inventors have conducted intensive studies in view of the aforementioned problems and clarified that a novel triglyceride wherein at least one fatty acid forming an ester bond with a hydroxy group of glycerol is 10-hydroxy-cis-12-octadecenoic acid, or an optical isomer thereof, is liquid at ambient temperature and has a good flavor, which resulted in the completion of the present invention.

That is, the present invention provides the following:
[1] A triglyceride in which at least one fatty acid forming an ester bond with a hydroxy group of glycerol is 10-hydroxy-cis-12-octadecenoic acid, or an optical isomer thereof.
[2] The triglyceride or an optical isomer thereof of the above-mentioned [1], wherein two fatty acids forming an ester bond with a hydroxy group of glycerol are each 10-hydroxy-cis-12-octadecenoic acid.
[3] The triglyceride or an optical isomer thereof of the above-mentioned [1], wherein three fatty acids forming an ester bond with a hydroxy group of glycerol are each 10-hydroxy-cis-12-octadecenoic acid.
[4] The triglyceride or an optical isomer thereof of the above-mentioned [1] or [2], wherein a fatty acid other than 10-hydroxy-cis-12-octadecenoic acid in the fatty acids forming an ester bond with a hydroxy group of glycerol is a fatty acid having a carbon number of 8-22.
[5] The triglyceride or an optical isomer thereof of the above-mentioned [4], wherein the fatty acid other than 10-hydroxy-cis-12-octadecenoic acid in the fatty acids forming an ester bond with a hydroxy group of glycerol is derived from an edible fat or oil.
[6] The triglyceride or an optical isomer thereof of the above-mentioned [4], wherein the fatty acid other than 10-hydroxy-cis-12-octadecenoic acid in the fatty acids forming an ester bond with a hydroxy group of glycerol is one or more kinds selected from the group consisting of linoleic acid, α-linolenic acid, γ-linolenic acid, stearidonic acid, oleic acid, stearic acid, arachidonic acid, eicosapentaenoic acid, docosahexaenoic acid, caprylic acid, capric acid, lauric acid, myristic acid, palmitic acid, arachidic acid, pulmitoleic acid, elaidic acid, mead acid and dihomo-γ-linolenic acid.

[7] The triglyceride or an optical isomer thereof of any of the above-mentioned [1]-[6], which is liquid at ambient temperature.

[8] An edible fat or oil comprising the triglyceride or an optical isomer thereof of any of the above-mentioned [1]-[7].

[9] A food or food additive comprising the triglyceride or an optical isomer thereof of any of the above-mentioned [1]-[7].

[10] A pharmaceutical composition comprising the triglyceride or an optical isomer thereof of any of the above-mentioned [1]-[7].

[11] An agent for the prophylaxis or treatment of a disease selected from the group consisting of obesity, diabetes, lipid metabolism abnormality, hyperlipidemia, fatty liver, ulcerative colitis, Crohn's disease, ulcer, irritable bowel syndrome and inflammatory diseases, comprising the triglyceride or an optical isomer thereof of any of the above-mentioned [1]-[7].

[12] A cosmetic or cosmetic additive comprising the triglyceride or an optical isomer thereof of any of the above-mentioned [1]-[7].

[13] A feed or feed additive comprising the triglyceride or an optical isomer thereof of any of the above-mentioned [1]-[7].

Effect of the Invention

According to the present invention, novel triglyceride or an optical isomer thereof can be provided. The triglyceride or an optical isomer thereof of the present invention is a derivative of HYA, liquid at ambient temperature, has a good flavor, and permits easy ingestion and easy handling.

In addition, in the triglyceride or an optical isomer thereof of the present invention, the ester bond of the triglyceride is hydrolyzed by lipase or the like in the body after ingestion to liberate HYA. Thus, superior physiological functions (lipid metabolism abnormality improving effect, action to increase intestinal immunity, intestinal inflammation suppressive action, etc.) as well as when HYA itself is ingested singly are expected to be exerted.

Therefore, the triglyceride or an optical isomer thereof of the present invention having the above-mentioned functions is industrially extremely useful because it can be utilized as edible fat or oil, and can also be utilized as every kind of food or food additive and further, utilized in various fields such as pharmaceutical product, cosmetic, feed and the like.

BRIEF DESCRIPTION OF THE DRAWINGS

FIG. 3 shows gas chromatography analysis chart of the fatty acid composition of the lipid extracted from each microorganism in Example 5.

DESCRIPTION OF EMBODIMENTS

The present invention is explained in detail in the following.

Definition

In the present specification, the "fatty acid" means a monovalent carboxylic acid of a straight chain or branched chain aliphatic hydrocarbon. The fatty acid may be a saturated fatty acid or a monovalent unsaturated fatty acid or polyvalent unsaturated fatty acid. In addition, the aliphatic hydrocarbon chain may be partially substituted by a hydroxy group or a carbonyl group. While the range of the carbon number of "fatty acid" is not particularly limited, it is preferably 6-26, more preferably 8-24, most preferably 8-22.

In the present specification, the "saturated fatty acid" means a fatty acid free of an unsaturated bond in the aliphatic hydrocarbon chain. In the present specification, the "monovalent unsaturated fatty acid" means a fatty acid having one unsaturated bond in the aliphatic hydrocarbon chain. In the present specification, moreover, the "polyvalent unsaturated fatty acid" means a fatty acid having not less than two unsaturated bonds in the aliphatic hydrocarbon chain.

In the present specification, the "acyl (group)" means an alkanoyl group or alkenoyl group derived from a fatty acid.

(The Compound of the Present Invention)

The compound of the present invention is triglyceride characterized in that at least one fatty acid forming an ester bond with a hydroxy group of glycerol is 10-hydroxy-cis-12-octadecenoic acid, or an optical isomer thereof, preferably, triglyceride wherein one fatty acid forming an ester bond with a hydroxy group of glycerol is 10-hydroxy-cis-12-octadecenoic acid, or an optical isomer thereof, or triglyceride wherein two fatty acids forming an ester bond with a hydroxy group of glycerol are each 10-hydroxy-cis-12-octadecenoic acid, or an optical isomer thereof.

The compound of the present invention is, specifically, a triglyceride represented by the following formula (I):

$$\begin{array}{c} \text{—OR}^1 \\ \text{—OR}^2 \\ \text{—OR}^3 \end{array} \quad (I)$$

wherein $R^1$, $R^2$ and $R^3$ are the same or different and each is an acyl group, at least one of which is a 10-hydroxy-cis-12-octadecenoyl group represented by the following formula (II):

(II)

wherein * is a binding position with an oxygen atom in a compound represented by the formula (I), or an optical isomer thereof (hereinafter sometimes to be referred to as compound (I)).

In compound (I) of the present invention, at least one of the acyl groups for $R^1$, $R^2$ or $R^3$ is a 10-hydroxy-cis-12-octadecenoyl group represented by the formula (II). The aforementioned 10-hydroxy-cis-12-octadecenoyl group may be bonded to any hydroxy group at the 1-position, the 2-position and the 3-position of glycerol in compound (I).

In the present invention, one or two acyl groups for $R^1$, $R^2$ or $R^3$ may be a 10-hydroxy-cis-12-octadecenoyl group, or every acyl group for $R^1$, $R^2$ or R may be a 10-hydroxy-cis-12-octadecenoyl group, and a compound wherein one or two acyl groups for $R^1$, $R^2$ or $R^3$ are each a 10-hydroxy-cis-12-octadecenoyl group is preferable.

While the kind of the acyl group other than the 10-hydroxy-cis-12-octadecenoyl group for $R^1$, $R^2$ or $R^3$ in compound (I) of the present invention is not particularly limited, an acyl group having a carbon number of 6-26 is preferable, an acyl group having a carbon number of 8-24 is more preferable, and an acyl group having a carbon number of 8-22 is particularly preferable.

To be specific, an acyl group derived from polyvalent unsaturated fatty acid such as 9,12-octadecadienoic acid (linoleic acid) [18:2,ω6], 6,9,12-octadecatrienoic acid (γ-linolenic acid) [18:3,ω6], 8,11,14-eicosatrienoic acid (dihomo-γ-linolenic acid) [20:3,ω6], 5,8,11,14-eicosatetraenoic acid (arachidonic acid) [20:4,ω6], 7,10,13,16-docosatetraenoic acid [22:4,ω6], 4,7,10,13,16-docosapentaenoic acid [22:5,ω6], 9,12,15-octadecatrienoic acid (α-linolenic acid) [18:3,ω3], 6,9,12,15-octadecatetraenoic acid (stearidonic acid) [18:4,ω3], 11,14,17-eicosatrienoic acid [20:3,ω3], 8,11,14,17-eicosatetraenoic acid [20:4,ω3], 5,8,11,14,17-eicosapentaenoic acid (eicosapentaenoic acid) [20:5,ω3], 7,10,13,16,19-docosapentaenoic acid [22:5,ω3], 4,7,10,13,16,19-docosahexaenoic acid (docosahexaenoic acid) [22:6,ω3], 6,9-octadecadienoic acid [18:2,ω9], 8,11-eicosadienoic acid [20:2,ω9], 5,8,11-eicosatrienoic acid (mead acid) [20:3,ω9], 9,11-conjugated linoleic acid [18:2], 10,12-conjugated linoleic acid [18:2], 9,11,13-conjugated linolenic acid [18:3], 8,10,12-conjugated linolenic acid [18:3], 9,11,15-conjugated linolenic acid [18:3], 10,12,15-conjugated linolenic acid [18:3], 6,9,11-conjugated linolenic acid [18:3], 6,10,12-conjugated linolenic acid [18:3] and the like; an acyl group derived from monovalent unsaturated fatty acid such as oleic acid (18:1,ω9), pulmitoleic acid (16:1,ω7), elaidic acid (18:1,ω9), eicosenoic acid (20:1,ω9), erucic acid (22:1,ω9), nervonic acid (24:1,ω9) and the like; an acyl group derived from saturated fatty acid such as caproic acid (6:0), caprylic acid (8:0), capric acid (10:0), lauric acid (12:0), myristic acid (14:0), palmitic acid (16:0), margaric acid (17:0), stearic acid (18:0), arachidic acid (20:0), behenic acid (22:0), lignoceric acid (24:0), cerotic acid (26:0) and the like can be mentioned. Among these, an acyl group derived from a fatty acid having a carbon number of 8-22 such as linoleic acid, α-linolenic acid, γ-linolenic acid, oleic acid, stearic acid, arachidonic acid, eicosapentaenoic acid, docosahexaenoic acid, caprylic acid, capric acid, lauric acid, myristic acid, palmitic acid, arachidic acid, pulmitoleic acid, elaidic acid, dihomo-γ-linolenic acid, stearidonic acid and mead acid and the like is particularly preferable.

As an acyl group other than a 10-hydroxy-cis-12-octadecenoyl group in compound (I) of the present invention, an acyl group derived from a fatty acid derived from edible fat or oil such as plant-derived fat or oil, animal-derived fat or oil, and the like can also be mentioned as a preferable acyl group.

In the present specification, the "acyl group derived from a fatty acid derived from edible fat or oil such as plant-derived fat or oil, animal-derived fat or oil, and the like" means a fatty acid derived from fat or oil obtained by extracting and purifying fat contained in plant or animal such as fish can be mentioned. Specifically, for example, linoleic acid, α-linolenic acid, γ-linolenic acid, stearidonic acid, oleic acid, stearic acid, arachidonic acid, eicosapentaenoic acid, docosahexaenoic acid, caprylic acid, capric acid, lauric acid, myristic acid, palmitic acid, arachidic acid, pulmitoleic acid, elaidic acid, mead acid, dihomo-γ-linolenic acid and the like can be mentioned.

When compound (I) of the present invention has two acyl groups other than a 10-hydroxy-cis-12-octadecenoyl group, they may be the same or different and may be bonded to any hydroxy group at the 1-position, the 2-position or the 3-position of glycerol.

The compound (I) of the present invention may be a mixture of two or more kinds of triglycerides of a triglyceride wherein one of the acyl groups for $R^1$, $R^2$ or $R^3$ is a 10-hydroxy-cis-12-octadecenoyl group, a triglyceride wherein two of the acyl groups for $R^1$, $R^2$ or $R^3$ are 10-hydroxy-cis-12-octadecenoyl groups, and a triglyceride wherein all of the acyl groups for $R^1$, $R^2$ or $R^3$ are 10-hydroxy-cis-12-octadecenoyl groups.

In addition, it may be a mixture of two or more kinds of triglyceride wherein one or two acyl groups for $R^1$, $R^2$ or R are each a 10-hydroxy-cis-12-octadecenoyl group.

When compound (I) of the present invention has an isomer such as optical isomer, stereoisomer, regio isomer and the like, any isomer and a mixture thereof are encompassed in compound (I) of the present invention.

When compound (I) of the present invention has optical isomers, the optical isomers can be each obtained as an optically pure compound by a known synthetic method, separation method (crystallization method, separation by high performance liquid chromatography using optically active column, enzyme method etc.) and the like. The optical isomers may be used in a mixed state, or optically pure compounds each obtained by separation may be used singly, or they may be used in combination.

The melting point of compound (I) of the present invention is not more than the melting point of HYA (about 25° C.). Compound (I) of the present invention is preferably liquid at a standard temperature, more preferably, liquid at ambient temperature. The standard temperature and ambient temperature here refer to the standard temperature (20° C.) and ambient temperature (15° C.-25° C.) defined in the Japanese Pharmacopoeia, 16th edition, General Rules, the Japanese Pharmacopoeia, 17th edition, General Rules. In addition, "about" here means±1° C.

(Production Method of Compound (I) of the Present Invention)

The production method of compound (I) of the present invention is not particularly limited. For example, a production method including a transesterification reaction of triglyceride and HYA or an ester form thereof or an activated form thereof (e.g., acid halide, active ester, acid anhydride etc.), or a simultaneous or sequential transesterification reaction of triglyceride and HYA and fatty acid other than HYA, or an ester form thereof or an activated form thereof (production method 1), and a production method including a reaction of glycerol and HYA or an activated form thereof (e.g., acid halide, active ester, acid anhydride etc.), or a simultaneous or sequential reaction of glycerol and HYA and fatty acid other than HYA, or an activated form thereof (e.g., acid halide, active ester, acid anhydride etc.) to form an ester bond with a hydroxy group of glycerol (esterification) (production method 2) can be mentioned. In the above-mentioned production methods, the presence of water in the reaction system may cause hydrolysis of compound (I) as the resultant product and may decrease the yield. Therefore, a reaction that proceeds even without water in the reaction system, like production method 1 and production method 2, is particularly preferably used. As the production method and reaction conditions, preferable ones can be selected in consideration of the stability of the starting compound and resultant product and the like, and plural production methods can also be combined. Furthermore, reaction steps such as protection, deprotection and the like can also be combined as appropriate. Furthermore, compound (I) can also be produced by a production method by oil synthesis utilizing accumulation of fats and oils by microorganisms (production method 3).

HYA used in each of the above-mentioned production methods can be prepared by the method described in patent document 2 and the like. As trilinolein and glycerol used in each of the above-mentioned production methods, commercially available products of Tokyo Chemical Industry Co., Ltd. and the like can be utilized as they are. As triglyceride other than trilinolein, commercially available products may be utilized, or may be prepared by an ester formation reaction of a hydroxy group of glycerol and fatty acid or an activated form thereof (e.g., acid halide, active ester, acid anhydride etc.) and utilized. The above-mentioned ester formation reaction can be performed by a method similar to production method 2.

The production method 1 of compound (I) of the present invention is explained below.

As the transesterification reaction of production method 1, any of enzymatic reaction and chemical reaction is used, and an enzymatic reaction is preferable since the reaction can be performed highly selectively under convenient and mild conditions.

The enzyme to be used in the transesterification reaction of production method 1 is not particularly limited as long as it an enzyme capable of converting at least one acyl group of triglyceride to a 10-hydroxy-cis-12-octadecenoyl group. For example, lipase, esterase and the like can be mentioned, and lipase is preferable. Lipase can be purchased as a commercially available product from Novozymes A/S, Amano Enzyme Inc., Meito Sangyo Co., Ltd., Sigma-Aldrich Co. LLC and the like.

In the enzymatic reaction of production method 1, the water content of the reaction substrate and solvent is desirably as small as possible so that the reaction substrate and triglyceride as a reaction resultant product will not be hydrolyzed. The reaction can be performed without solvent or in various non-aqueous solvents (e.g., non-polar solvents such as n-heptane, n-hexane, isooctane and the like), and reaction without solvent is more preferable. It is further preferable to replace the gaseous matter in the reaction system with an inert gas such as nitrogen gas, argon gas and the like to suppress moisture contamination of the substrate and solvent to be used.

The reaction temperature of production method 1 varies depending on the presence or absence of the solvent, the kind of solvent when a solvent is used, the kind of enzyme, the kind of triglyceride and fatty acid as reaction substrates and the like. It is generally 4° C.-100° C., preferably 20° C.-70° C., more preferably 30° C.-50° C.

The reaction time of production method 1 varies depending on the presence or absence of the solvent, the kind of solvent when a solvent is used, the kind of enzyme, the kind of triglyceride and fatty acid as reaction substrates and the like. It is generally 1 hr-168 hr, preferably 5 hr-48 hr.

As the triglyceride to be used as a reaction substrate in production method 1, any can be used without particular limitation as long as compound (I) of the present invention can be obtained by a transesterification reaction with HYA. For example, triglycerides such as trilinolein having three 9,12-octadecadienoyl groups, triolein having three 9-octadecenoyl groups and the like can be used preferably as starting materials since they are commercially available and easily obtained. In addition, edible fats and oils can be used preferably as starting materials since they are commercially available and easily obtained.

The amount of HYA to be used in production method 1, or the total amount of HYA and fatty acid other than HYA to be used is preferably 10 wt % to 500 wt %, particularly preferably 20 wt % to 100 wt %, relative to triglyceride. When HYA, and each ester form or each activated form of fatty acid other than HYA are used as starting materials, the above-mentioned amounts after conversion to the amount of HYA or the amount of fatty acid other than HYA can be used.

The amount of enzyme to be used in production method 1 is preferably 1 wt % to 100 wt %, more preferably 1 wt % to 50 wt %, particularly preferably 1 wt % to 20 wt %, relative to triglyceride.

The production method 2 of compound (I) of the present invention is explained below.

The esterification step in production method 2 can be performed using an enzymatic reaction or chemical reaction, and an enzymatic reaction is preferably used since the reaction operation is convenient and the reaction conditions are mild.

The enzyme to be used in the esterification of glycerol of production method 2 is not particularly limited as long as it is capable of conversion to compound (I) of the present invention. For example, lipase, esterase and the like can be mentioned, and lipase is preferable.

In the esterification step of production method 2, the water content of the reaction substrate and solvent is desirably as small as possible so that triglyceride as a reaction resultant product will not be hydrolyzed. The reaction can be performed without solvent or in various non-aqueous solvents (e.g., non-polar solvents such as n-heptane, n-hexane, isooctane and the like), and reaction without solvent is more preferable. Furthermore, the esterification reaction may be accelerated by removing water from the reaction system to shift the reaction equilibrium or the reaction can also be carried out under reduced pressure to reduce the water content of the reaction substrate and solvent to be used.

The reaction temperature of production method 2 varies depending on the presence or absence of the solvent, the kind of solvent when a solvent is used, the kind of enzyme, the kind of fatty acid or an activated form thereof as reaction substrates and the like. It is generally 4° C.-100° C., preferably 20° C.-70° C., more preferably 30° C.-50° C.

The reaction time of production method 2 varies depending on the presence or absence of the solvent, the kind of solvent when a solvent is used, the kind of enzyme, the kind of fatty acid or an activated form thereof as reaction substrates and the like. It is generally 1 hr-168 hr, preferably 5 hr-120 hr.

The amount of HYA to be used as the reaction substrate in production method 2, or the total amount of HYA and fatty acid other than HYA to be used is preferably 1000 wt %-10000 wt %, more preferably 1500 wt %-8000 wt %, particularly preferably 2000 wt %-5000 wt %, relative to glycerol. When HYA, and each activated form of fatty acid other than HYA are used as starting materials, the above-mentioned amounts after conversion to the amount of HYA or the amount of fatty acid other than HYA can be used.

The amount of enzyme relative to that of glycerol to be used as a reaction substrate in production method 2 is preferably 1 wt %-100 wt %, more preferably 10 wt %-90 wt %, particularly preferably 30 wt %-80 wt %.

The enzyme to be used for the enzymatic reaction used in the above-mentioned production methods 1 and 2 may be immobilized by various carriers or may be of a free type.

The immobilized ones are more preferable since they are highly active even in an anhydrous reaction system and also in a reaction system with a small amount of water, and can be recovered and used repeatedly. The above-mentioned enzymes may be purified or crude products. The enzymes may be expressed in bacteria such as *Escherichia coli* or the like and the bacterial cells themselves may be used or culture broth of the bacterial cells may be used.

In the production method by oil synthesis using microorganisms (production method 3), the microorganism to be used for the production is exemplified by Zygomycetes belonging to the *Basidiobolus* genus (*Basidiobolus magnus, Basidiobolus ranarum, Basidiobolus haptosporus* etc.), fungus such as oyster mushroom (*Pleurotus ostreatus*) and the like and the like can be mentioned. The type of microorganism is not questioned as long as it has an ability to synthesize triglycerides.

(Edible Fats and Oils in the Present Invention)

The present invention provides edible fats and oils containing compound (I) of the present invention (hereinafter to be also referred to as "edible fats and oils the present invention").

That is, compound (I) of the present invention can singly provide edible fats and oils, or blended with other edible fats and oils to give edible fats and oils. While the content of compound (I) of the present invention in the edible fats and oils of the present invention is not particularly limited, it is generally not less than 5 wt %, preferably not less than 20 wt %, more preferably not less than 50 wt %, relative to the total amount of edible fats and oils. It is particularly preferable to use edible fats and oils singly because superior flavor and physiological function can be obtained.

The edible fats and oils of the present invention may contain, for example, general components (food additive etc.), which are used for edible fats and oils, as long as the characteristics of the present invention are not impaired. Examples of these components include emulsifier, oxidation/degradation inhibitor, antifoaming agent, crystal adjuster and the like.

Examples of the emulsifier include glycerol fatty acid ester, polyglycerol fatty acid ester, sucrose fatty acid ester, polyglycerol condensed ricinoleic acid ester, sorbitan fatty acid ester, propyleneglycol fatty acid ester, polyoxyethylene sorbitan fatty acid ester, organic acid monoglyceride and the like.

Examples of the oxidation/degradation inhibitor include tocopherols, flavone derivative, gallic acid derivative, catechin and ester thereof, lignans (e.g., sesamine and the like), fukiic acid, sesamol, terpenes and the like.

Examples of the antifoaming agent include silicone oil and the like.

Examples of the crystal adjuster include triacylglycerol other than compound (I) of the present invention, diacylglycerol, monofatty acid glyceryl, heptafatty acid decaglyceryl, decafatty acid decaglyceryl, waxes, sterol esters and the like.

In addition, spice, colorant and the like can also be added. Examples of the spice include capsaicin, anethole, eugenol, cineol, zingerone and the like. Examples of the colorant include carotene, astaxanthin and the like.

Furthermore, the edible fats and oils of the present invention may also contain various nutrients (carbohydrates, protein etc.), various vitamins (vitamin A, vitamin $B_1$, vitamin $B_2$, vitamin $B_6$, vitamin C, vitamin D, vitamin E, vitamin K etc.), various minerals (magnesium, zinc, iron, sodium, potassium, selenium etc.) and the like as necessary.

(Food or Food Additive of the Present Invention)

The present invention provides a food or food additive containing compound (I) of the present invention (hereinafter to be also referred to as "food or food additive of the present invention" in the present specification).

The food or food additive of the present invention is not particularly limited as long as it is in an orally ingestable form such as solution, suspension, emulsion, gel, powder, solid molded product and the like.

Specific examples of the food or food additive of the present invention include supplement (powder, granule, soft capsule, hard capsule, tablet, chewable tablet, quick-integrating tablet, syrup, liquid etc.), drinks (carbonated drinks, lactic drinks, sports drinks, fruit juice drinks, vegetable drinks, soymilk drink, coffee drinks, tea drinks, powder drinks, concentration drinks, nutritional beverage, alcohol drinks etc.), confectionery (gummi candy, jelly, gum, chocolate, cookie, candy, caramel candy, Japanese confectionery, snack food etc.), table-ready foods (instant noodles, retort food, canned food, microwave food, instant soup, miso soup, freeze-dry food etc.), fats and oils food (mayonnaise, dressing, butter, cream, margarine etc.), wheat flour product (bread, pasta, noodle, cake mixture, breadcrumbs etc.), seasoning (sauce, tomato processing seasoning, flavor seasoning, mixture for cooking, seasoning soy sauce etc.), and processed meat product (meat ham, sausage etc.) and the like.

The content of compound (I) of the present invention in the food or food additive of the present invention is 5 wt %-90 wt %, preferably 10 wt %-80 wt %, more preferably 20 wt %-70 wt %, relative to the total amount of the food or food additive.

The daily ingestion amount of the food or food additive of the present invention is appropriately determined according to the age of the subject who ingests the food or food additive, symptoms and conditions and the severity thereof expected to be improved by the ingestion, dosage form of food and the like, and the like. It is preferable that the ingestion amount of compound (I) of the present invention is set to such amount as will be the below-mentioned daily ingestion amount after conversion to HYA.

The food or food additive of the present invention can be blended with various nutrients (carbohydrates, protein etc.), various vitamins (vitamin A, vitamin $B_1$, vitamin $B_2$, vitamin $B_6$, vitamin C, vitamin D, vitamin E, vitamin K etc.), various minerals (magnesium, zinc, iron, sodium, potassium, selenium etc.), dietary fiber, food with reported physiological function (royal jelly, propolis, *agaricus* etc.) and the like as necessary.

In addition, the food or food composition of the present invention can contain, as necessary, general food additives, for example, emulsifier (glycerol fatty acid ester, sucrose fatty acid ester etc.), thickening stabilizer (pectin, sodium carboxymethylcellulose etc.), antioxidant (mixed vitamin E, sodium erythorbate etc.), preservative (sodium benzoate, sorbic acid etc.), gloss agent (shellac, beeswax etc.), sweetener (xylitol, aspartame etc.), acidulant (citric acid, malic acid etc.), bittering agent (caffeine, naringin etc.), seasoning (sodium L-glutamate, disodium 5'-inosinate etc.), colorant (*gardenia* yellow dye, red No. 2 etc.), flavor (orange flavor, vanillin etc.), manufacturing agent (brine, binding agent etc.) and the like.

The food or food additive of the present invention can be prepared by a general production method by adding the above-mentioned various nutrients, various vitamins and the like, and general food additives as necessary to compound (I) of the present invention.

The above-mentioned edible fats and oils, and food or food additive of the present invention also encompasses those classified in the health food, functional food, food with health claims (e.g., food for specified health uses, foods with function claims etc.), food for special dietary uses (e.g., food for patient etc.), edible fats and oils and foods with a disease risk reduction indication and the like.

Examples of the "disease risk reduction indication" is, for example, an indication that it is for treating, improving, suppressing and/or preventing diseases whose symptoms can be improved by HYA. Therefore, the edible fats and oils, food or food additive of the present invention can be provided as edible fats and oils, food or food additive with an indication that it is for the improvement and/or prophylaxis of the diseases whose symptoms can be improved by HYA; for example, obesity, diabetes, lipid metabolism abnormality, hyperlipidemia, fatty liver, inflammatory bowel disease (ulcerative colitis, Crohn's disease, pseudomembranous enteritis etc.), ulcer, irritable bowel syndrome, and various other inflammatory diseases (e.g., gout, arthritis, polyneuritis, polyneuroradiculitis, hepatitis, bronchitis, pneumonia, nephritis, cystitis, periodontal disease, dermatitis, atopic dermatitis etc.).

(The Pharmaceutical Composition of the Present Invention)

The present invention provides a pharmaceutical composition containing compound (I) of the present invention (hereinafter to be also referred to as "the pharmaceutical composition of the present invention" in the present specification).

The pharmaceutical composition of the present invention can be used as a prophylactic agent for preventing, or a therapeutic agent for treating, improving or suppressing diseases whose symptoms can be improved by HYA, in animals, for example, obesity, diabetes, lipid metabolism abnormality, hyperlipidemia, fatty liver, inflammatory bowel disease (ulcerative colitis, Crohn's disease, pseudomembranous enteritis etc.), ulcer, irritable bowel syndrome, and various other inflammatory diseases (e.g., gout, arthritis, polyneuritis, polyneuroradiculitis, hepatitis, bronchitis, pneumonia, nephritis, cystitis, periodontal disease, dermatitis, atopic dermatitis etc.).

As used herein, the "animal" includes mammals such as human, dog, cat, rabbit, hamster, rat, mouse, bovine, swine, sheep, horse, donkey, camel and the like.

The pharmaceutical composition of the present invention is not particularly limited, and can be provided, for example, as an oral preparations in various dosage forms such as powder, granule, pill, soft capsule, hard capsule, tablet, chewable tablet, quick-integrating tablet, syrup, liquid, suspension, emulsion and the like; and a parenteral preparation such as suppository, ointment, cream, gel, adhesive preparation, inhalant, injection and the like.

The pharmaceutical composition of the present invention can be produced by adding various additives as necessary to compound (I) of the present invention and according to a general formulation means, for example, the methods described in the Japanese Pharmacopoeia 16th edition Preparation General Rules [2] Monographs for Preparations, the Japanese Pharmacopoeia 17th edition Preparation General Rules [3] Monographs for Preparations and the like, and the like.

In the present invention, the additives that can be used for formulation are not particularly limited. For example, animal and plant fats and oils such as soybean oil, safflower oil, olive oil, germ oil, sunflower oil, beef tallow, sardine oil and the like; polyhydric alcohols such as polyethylene glycol, propylene glycol, glycerol, sorbitol and the like; surfactants such as sorbitan fatty acid ester, sucrose fatty acid ester, glycerol fatty acid ester, polyglycerol fatty acid ester and the like; solvents such as purified water, sterile purified water, water for injection, physiological saline, ethanol, isopropanol and the like; excipients such as lactose, starch, crystalline cellulose, D-mannitol, soybean lecithin, gum arabic, sorbitol solution, starch syrup and the like; binders such as pregelatinized starch, carboxymethylcellulose, hydroxypropylcellulose, shellac and the like; disintegrants such as crospovidone, povidone, dextrin and the like; lubricants such as magnesium silicate, aluminum stearate, talc and the like; sweetening agents such as aspartame, licorice extract, saccharin sodium and the like; colorants such as yellow iron oxide, brown iron oxide, black iron oxide, Food blue No. 1, Food Red No. 2 and the like; pH adjusters such as hydrochloric acid, citric acid, sodium citrate, potassium hydroxide, sodium hydroxide and the like; flavors such as bitter essence and the like and the like can be mentioned.

When a liquid preparation is produced, a solid preparation to be used by dissolving or suspending in water or other appropriate solvent when in use may be produced. Tablets and granules may be coated by a well-known method.

In the pharmaceutical composition of the present invention, as long as the effect of the present invention is not impaired, a therapeutic drug for the above-mentioned diseases that can be improved or prevented by the pharmaceutical composition of the present invention may be used in combination with compound (I) of the present invention.

Examples of the drug that can be used in combination with the pharmaceutical composition of the present invention (hereinafter to be also referred to as "concomitant drug" in the present specification) include therapeutic drugs for diabetes such as sulfonylurea (tolbutamide, glyclopyramide, glybuzole, glimepiride etc.), biguanide (metformin hydrochloride etc.), α-glucosidase inhibitor (voglibose, acarbose etc.), thiazolidine derivative (pioglitazone hydrochloride etc.) and the like; therapeutic drugs for hyperlipidemia such as statins (pravastatin sodium, simvastatin, pitavastatin calcium etc.), anion exchange resin (colestyramine, colestimide etc.), fibrates (clofibrate, clinofibrate etc.), nicotinic acids (nicotinic acid tocopherol, nicomol etc.) and the like; therapeutic drugs for inflammatory bowel diseases (Crohn's disease, ulcerative colitis, pseudomembranous enteritis etc.) such as salicylic acid preparation (mesalazine etc.), sustainable sulfonamide (salazosulfapyridine etc.), adrenal cortical steroid (betamethasone, predonisolone etc.), molecular-targeted therapeutic drug (infliximab, adalimumab etc.), immunosuppressant (azathioprine etc.) and the like; therapeutic drugs for irritable bowel syndrome such as anticholinergic drug (pipethanate hydrochloride, mepenzolate bromide etc.), gastrointestinal motility regulating agents (trimebutine etc.), synthesized polymer compound (polycarbophil calcium etc.), *lactobacillus* preparation and the like; therapeutic drugs for gout such as prophylactic drug for gout attack (colchicine etc.), uricosuric drug (probenecid, bucolome, benzbromarone etc.), uric acid synthesis inhibitor (allopurinol etc.) and the like; therapeutic drugs for arthritis, neuritis such as non-steroidal antiinflammatory agents (mefenamic acid, ketoprofen, diclofenac sodium etc.), biological active drug (cyclosporine etc.) and the like; therapeutic drugs for hepatitis such as interferon preparation (interferon β, interferon α-2a etc.), anti-hepatitis virus drug (ribavirin, lamivudine etc.), liver function improvement drug (glycyrrhizin preparation, glucuronic acid, tiopronin etc.) and the like; therapeutic drugs for bronchitis such as β-agonist (ephedrine hydrochloride, dl-methylephedrine hydrochloride, trimetoquinol hydrochloride etc.), theophyllines (diprophylline, aminophylline etc.), anticholinergic drug (thiotropium bromide hydrate etc.) and the like; therapeutic drugs for pneumonia such as macrolide antibiotics (clarithromycin, azithromycin etc.), newquinolone antibiotics (levofloxacin, garenoxacin etc.) and the like; therapeutic drugs for nephritis such as angiotensin converting enzyme inhibitor (enalapril maleate, delapril hydrochloride etc.), angiotensin II receptor antagonists (losartan potassium, candesartan cilexetil etc.) and the like; therapeutic drugs for cystitis such as newquinolone antibiotics (ofloxacin, levofloxacin, norfloxacin etc.), penicillin antibiotics (amoxicillin, ampicillin, cloxacillin etc.), cephem antibiotics (cefcapene pivoxil hydrochloride, cefotiam hexetil hydrochloride etc.), chinese medicine (hatimi-ziôgan, Umbellate Fungus Decoction etc.) and the like; therapeutic drugs for periodontal disease such as cephem antibiotics (cephalexin etc.), antimicrobial agent (benzethonium chloride, chlorhexidine hydrochloride etc.) and the like; therapeutic agents for dermatitis, atopic dermatitis such as non-steroidal antiinflammatory agents (bufexamac, ufenamate etc.), antipruritic drug (Crotamiton etc.) and the like; therapeutic agents for atopic dermatitis such as immunomodulative drug (tacrolimus hydrate etc.) and the like, and the like.

When the pharmaceutical composition of the present invention is produced as a parenteral preparation such as injection and the like, while the composition is not particularly limited, for example, it is preferably administered intravenously, intraperitoneally, intramuscularly, subcutaneously, transdermally, intra-articularly, intrasynovially, intramedullary, sublingually, intraorally and the like, particularly preferably intravenously or intraperitoneally. The intravenous administration may be any of drip administration and bolus administration.

The content of compound (I) of the present invention in the pharmaceutical composition of the present invention is 5 wt %-100 wt %, preferably 10 wt %-90 wt %, more preferably 20 wt %-80 wt %, relative to the total amount of the pharmaceutical composition of the present invention.

The dose of the pharmaceutical composition of the present invention can be appropriately determined according to the kind, age and body weight, symptom and severity of the animal to be the subject of administration, the dosage form and administration method of the pharmaceutical composition, the kind of the concomitant drug and the like. For example, when the pharmaceutical composition of the present invention is orally administered to human, it can be administered at 0.02 mg/kg body weight-100 mg/kg body weight, preferably 0.2 mg/kg body weight-50 mg/kg body weight, as the total amount converted to HYA as the active ingredient, to an adult daily. In addition, when the pharmaceutical composition is parenterally administered to human, it can be administered at 0.002 mg/kg body weight-50 mg/kg body weight, preferably 0.02 mg/kg body weight-50 mg/kg body. The aforementioned dose can be administered once a day or in several portions (2-5 times) for both the oral administration and parenteral administration.

In addition, the dosing period of the pharmaceutical composition of the present invention can be appropriately determined according to the condition, symptom and severity and the like of the animal that receives administration, and is generally 1 day-90 days, preferably 7 days-30 days.

(The Cosmetics or Cosmetics Additive of the Present Invention)

The present invention provides cosmetics or cosmetics additive containing compound (I) of the present invention (hereinafter to be referred to as "cosmetics or cosmetics additive of the present invention" in the present specification).

The cosmetics of the present invention can be prepared by adding various additives as necessary to compound (I) of the present invention, and according to the production method of the above-mentioned pharmaceutical composition.

The cosmetics of the present invention can be produced as cosmetics having various shapes such as skin cosmetics such as cream, gel, milky lotion, serum, toner, microemulsion essence, facial mask and the like; makeup cosmetics such as foundation, lip rouge, eye shadow, cheek color and the like; cleaning cosmetics such as cleansing oil, cleansing cream and the like; hair cosmetics such as shampoo, conditioner and the like; bathing powder and the like.

The cosmetics of the present invention may contain additives, which are generally used for cosmetics, as long as the characteristics of the present invention are not impaired. Examples thereof include active ingredients of antiwrinkle, anti-aging agent, anti-inflammatory agent, skin damage inhibitor, cell activator and wound healing agent, whitening agent and the like, oil (animal and plant fats and oils, wax, ester, higher fatty acid, higher aliphatic alcohol etc.), surfactant, solvent, thickener, humectant, antioxidant, preservative, pH adjuster, pigment, flavor and the like.

The cosmetic additive of the present invention can be produced as a form such as oil, suspension, milk, paste, powder, granule and the like by adding, as necessary, the above-mentioned oil, surfactant, solvent, thickener, pigment and the like to compound (I) of the present invention, and according to the above-mentioned production method of the pharmaceutical composition.

The content of compound (I) of the present invention in the cosmetics or cosmetics additive of the present invention is 5 wt %-70 wt %, preferably 10 wt %-60 wt %, more preferably 20 wt %-50 wt %, relative to the total amount of the cosmetics and the like of the present invention.

(The Feed or Feed Additive of the Present Invention)

The present invention provides a feed or feed additive containing compound (I) of the present invention (hereinafter to be also referred to as "feed or feed additive of the present invention" in the present specification).

The feed or feed additive of the present invention can be produced as a form such as oil, suspension, emulsion, gel, powder, granule, tablet and the like.

As the feed or feed additive of the present invention, pet food, farming or aquaculture feed additive and the like can be mentioned.

The feed or feed additive of the present invention can be prepared according to a general method by mixing compound (I) of the present invention with filler substances, dilution substances and the like for feed.

The filler substances, dilution substances and the like for feed can be used without particular limitation as long as the characteristics of the present invention are not impaired. For example, polysaccharides such as gum arabic, carrageenan, agar, xanthan gum, chitosan, cellulose, locust bean gum and the like; monosaccharides or disaccharides such as glucose, lactose, maltose, sucrose and the like; sugar alcohols such as glycerol, sorbitol, D-mannitol and the like; proteins such as albumin, casein, gluten, gelatin and the like; grain powders such as toasted soybean flour, wheat flour, soy flour, corn flour and the like; yeasts such as torula yeast, bread yeast, beer yeast and the like; fats and oils such as hydrogenated oil, plant-derived fats and oils, animal-derived fats and oils and the like; clay minerals such as kaolin, zeolite, talc, vermiculite, bentonite and the like; silicic acids such as diatomaceous earth, hydrated silicon dioxide, silicic acid, light anhydrous silicic acid, silicic anhydride, calcium silicate, magnesium silicate and the like or a salt thereof; hydrocarbons such as light liquid paraffin, liquid paraffin and the like; wax such as carnauba wax and the like, and the like can be mentioned.

Furthermore, the feed or feed additive of the present invention can contain, as long as the characteristics of the present invention are not impaired, additives for nutrition component supplementation, amino acids such as glycine, DL-alanine, sodium L-glutamate and the like; vitamins such as L-ascorbic acid, ergocalciferol, thiamine hydrochloride, cholecalciferol, vitamin A powder, vitamin D powder, riboflavin and the like; minerals such as potassium chloride, ferric citrate, calcium gluconate and the like; and dyes such as astaxanthin, canthaxanthin and the like.

The content of compound (I) of the present invention in the feed or feed additive of the present invention is 1 wt %-70 wt %, preferably 3 wt %-50 wt %, more preferably 5 wt %-30 wt %, relative to the total amount of the feed and the like of the present invention.

EXAMPLES

The present invention is explained in detail in the following by referring to Examples and Experimental Examples, which are not to be construed as limitative. The invention may be changed within the scope of the present invention.

In the following Examples, proton nuclear magnetic resonance ($^1$H NMR) spectrum was measured using AVANCE III 500 manufactured by Bruker and deuterochloroform as a solvent. The data of $^1$H NMR are reported as chemical shift (δ ppm), multiplicity (s=singlet, d=doublet, t=triplet, q=quartet, m=multiplet, dd=double doublet, dt=double triplet, tt=triple triplet, brs=broad singlet, sep=septet), coupling constant (Hz), integration and allocation.

High resolution mass spectrometry was performed using high-speed liquid chromatograph mass spectrometer (LCMS) (LCMS-2020) manufactured by Shimadzu Corporation.

Melting point (mp) was measured using melting point measuring instrument (MP-J3) manufactured by Anatec Yanaco Inc.

In the following Examples, compound (I) of the present invention was produced based on the above-mentioned production method 1. Trilinolein used as a reaction substrate for the production of compound (I) of the present invention is commercially available (manufactured by Tokyo Chemical Industry Co., Ltd.), and HYA was prepared according to the method described in patent document 2 and used. Other starting compounds and reagents were commercially available products used as they were, or can be produced according to a method known per se, or a method analogous thereto.

[Example 1] Di(cis, cis-9,12-octadecadienoyl)(10-hydroxy-cis-12-octadecenoyl)glycerol In a 100 mL reaction vessel (medium bottle) were placed trilinolein (10 g), transesterification enzyme (lipase) (Novozymes A/S, Lipozyme RMIM, 1 g) and HYA (5 g), the gaseous phase of the reaction system was replaced with nitrogen gas, and the mixture was stirred at 40° C. for 72 hr. To the reaction mixture was added 0.5N aqueous sodium hydroxide solution, and the mixture was extracted with ethyl acetate. The organic layer was concentrated to give a mixture (8.0 g) of triglyceride containing unreacted trilinolein or an optical isomer thereof. The obtained mixture was isolated and purified by moderate-pressure silica gel chromatography ("Flash automatic purification apparatus Isolera One", manufactured by Biotage AB, column: "SNAP Ultra", manufactured by Biotage AB, eluted with hexane:ethyl acetate=90:10-0:100) to give di(cis, cis-9,12-octadecadienoyl) (10-hydroxy-cis-12-octadecenoyl)glycerol (3.5 g).

melting point: not more than −20° C.;
$^1$H NMR (CDCl$_3$, 500 MHz): (δ) ppm: 0.89 (t, 9H, J=7.0 Hz), 1.30 (m, 44H), 1.46 (m, 2H), 1.61 (m, 6H), 2.05 (dt, 10H, J=6.8, 7.0 Hz), 2.21 (dd, 2H, J=6.6, 6.6 Hz), 2.31 (m, 6H), 2.77 (dd, 4H, J=6.6, 6.6 Hz), 3.61 (m, 1H), 4.14 (d, 1H, J=11.9 Hz), 4.15 (d, 1H, J=10.9 Hz), 4.29 (d, 1H, J=11.9 Hz), 4.30 (d, 1H, J=11.9 Hz), 5.26 (tt, 1H, J=4.4, 5.8 Hz), 5.36 (m, 9H), 5.57 (dt, 1H, J=7.3, 10.9 Hz); MS(ESI): M$^+$ 897.

[Example 2] Di(10-hydroxy-cis-12-octadecenoyl) (cis, cis-9,12-octadecadienoyl)glycerol In the same manner as in Example 1, a mixture (mixture of triglyceride containing unreacted trilinolein or an optical isomer thereof) (8.0 g) obtained by transesterification reaction was isolated and purified by moderate-pressure silica gel chromatography to give di(10-hydroxy-cis-12-octadecenoyl) (cis, cis-9,12-octadecadienoyl)glycerol (0.53 g).

melting point: 7.2-7.8° C.;
$^1$H NMR (CDCl$_3$, 500 MHz): (δ) ppm: 0.89 (t, 9H, J=7.0 Hz), 1.30 (m, 46H), 1.46 (m, 4H), 1.59 (m, 6H), 2.05 (dt, 8H, J=7.1, 7.3 Hz), 2.21 (dd, 4H, J=6.5, 6.5 Hz), 2.31 (m, 6H), 2.77 (dd, 2H, J=6.6, 6.6 Hz), 3.61 (m, 2H), 4.14 (d, 1H, J=11.9 Hz), 4.15 (d, 1H, J=11.9 Hz), 4.28 (d, 1H, J=11.9 Hz), 4.30 (d, 1H, J=11.9 Hz), 5.26 (tt, 1H, J=4.4, 5.9 Hz), 5.36 (m, 6H), 5.57 (dt, 2H, J=7.3, 10.9 Hz); MS(ESI): M$^+$ 915.

[Example 3] Tri(10-hydroxy-cis-12-octadecenoyl)glycerol

In the same manner as in Example 1, a mixture (mixture of triglyceride containing unreacted trilinolein or an optical isomer thereof) (8.0 g) obtained by transesterification reaction was isolated and purified by moderate-pressure silica gel chromatography to give tri(10-hydroxy-cis-12-octadecenoyl)glycerol (0.068 g).

melting point: 20.0-21.2° C.;
$^1$H NMR (CDCl$_3$, 500 MHz): (δ) ppm: 0.89 (t, 9H, J=6.9 Hz), 1.30 (m, 48H), 1.46 (m, 6H), 1.61 (m, 6H), 2.05 (dt, 6H, J=7.3, 7.5 Hz), 2.21 (dd, 6H, J=6.7, 6.7 Hz), 2.31 (m, 6H), 3.61 (tt, 3H, J=5.8, 6.2 Hz), 4.14 (d, 1H, J=11.9 Hz), 4.15 (d, 1H, J=11.9 Hz), 4.29 (d, 1H, J=11.9 Hz), 4.30 (d, 1H, J=11.9 Hz), 5.26 (tt, 1H, J=4.4, 5.9 Hz), 5.40 (dt, 3H, J=7.5, 10.8 Hz), 5.57 (dt, 3H, J=7.3, 10.9 Hz); MS(ESI): M$^+$ 993.

[Comparative Example 1] Trilinolein

As Comparative Example 1, trilinolein as the above-mentioned commercially available product (manufactured by Tokyo Chemical Industry Co., Ltd.) was used.

[Comparative Example 2]
10-Hydroxy-cis-12-octadecenoic Acid (HYA)

As Comparative Example 2, HYA prepared according to the method described in patent document 2 was used.

Experimental Example 1

Whether compounds (I) of the present invention of Examples 1-3, trilinolein of Comparative Example 1 and HYA of Comparative Example 2 are liquid or solid at standard temperature (about 20° C.) was confirmed by visual observation.

As a result, as shown in Table 1 below, it was found that all were liquid at standard temperature (about 20° C.) except HYA of Comparative Example 2, the melting point became lower by converting HYA to triglyceride, and triglyceride having at least one 10-hydroxy-12-cis-octadecenoyl group is in a liquid state at standard temperature (about 20° C.).

Experimental Example 2

A sensory evaluation of the flavor of compounds (I) of the present invention of Examples 1-3, trilinolein of Comparative Example 1 and HYA of Comparative Example 2 was performed by 10 panelists (hereinafter to be referred to as taste test). The panelists ingested 5 mg of a sample (sample name was kept secret to the panelists during the test), evaluated five tastes (umami taste, bitter taste, sour taste, saltiness, sweetness) respectively for the strength, acridity and oil odor, and made total evaluation.

Each evaluation was marked in the following 5 grades.

Five tastes (umami taste, bitter taste, sour taste, saltiness, sweetness):
Strong (5 points)-weak (1 point)
Acridity: weak (5 points)-strong (1 point)
Oil odor: weak (5 points)-strong (1 point)
Total evaluation: delicious (5 points)-brackish (1 point)

As a result, as shown in Table 1 below, it was found that compounds (I) of the present invention improved umami taste and sweetness as compared to trilinolein of Comparative Example 1 and HYA of Comparative Example 2, and reduced the bitter taste than HYA of Comparative Example 2. It was also shown that acridity was reduced by converting HYA to triglyceride. Furthermore, it was shown that compounds (I) of the present invention are weak in oil odor and superior in the total evaluation as compared to trilinolein and HYA.

From the results of Experimental Examples 1, 2, it could be confirmed that compound (I) of the present invention is liquid at standard temperature (about 20° C.), does not have acridity but has strong umami taste.

[Example 4] Production of Compound (I) of the Present Invention Having Triglyceride of Edible Fat or Oil as Substrate In a 15 mL screw test tube were placed respective edible fats and oils (each 0.4 g: linseed oil, canola oil, safflower oil, soybean oil, corn oil, olive oil, cottonseed oil, coconut oil), transesterification enzyme (lipase) (Novozymes A/S, Novozym 40086, 0.1 g), HYA (0.6 g) and hexane (1 mL), the gaseous phase of the reaction system was replaced with nitrogen gas, and the mixture was stirred at 40° C. for 1-4 hr.

In Example 4, after reaction for 1 hr, a portion of the reaction mixture was subjected to high performance liquid chromatography (system controller: "CBM-20A", pump: "LC-10ADVP" (2 pumps), column oven: "CTO-10AVP", autosampler: "SIL-20ACHT", detector: "ELSD-LTII", above manufactured by Shimadzu Corporation, eluted with hexane:ethyl acetate=90:10-50:50), and component analysis was performed. As a result, a peak (peak having the same retention time as that of triglyceride containing HYA as one constituent fatty acid) not seen before the reaction was detected in all edible fats and oils used as the substrate.

Figure 1:
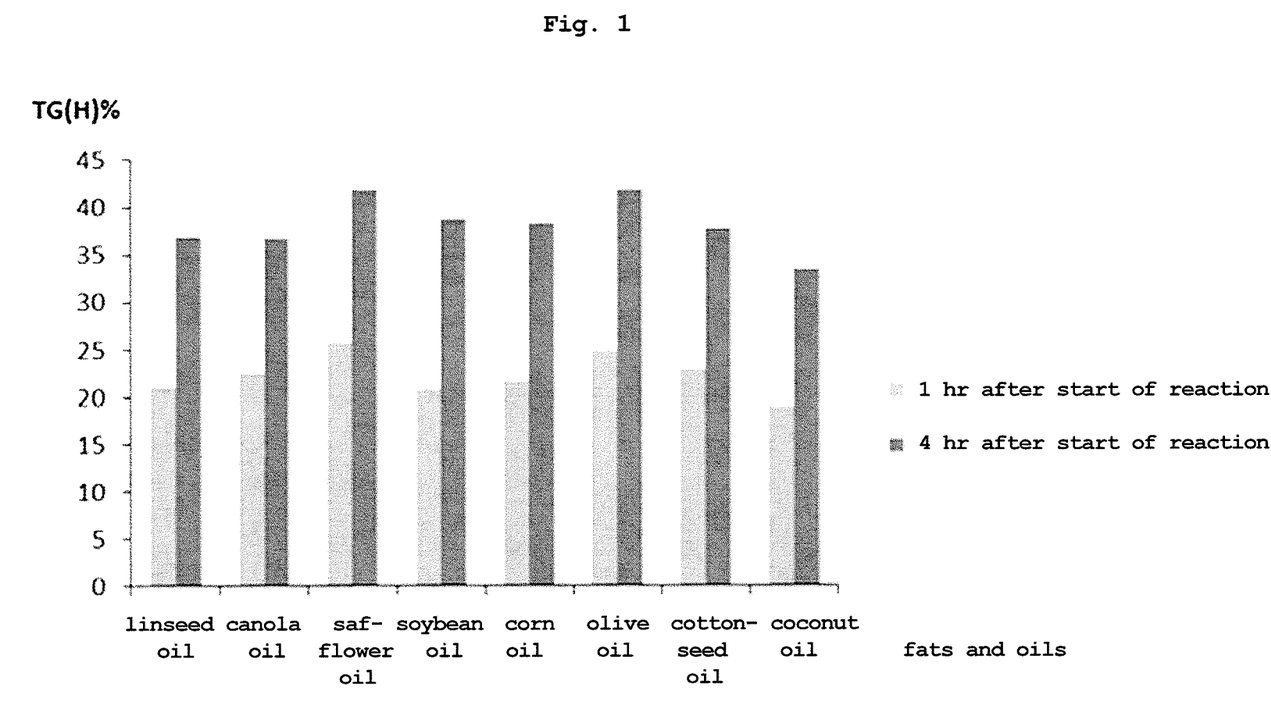
FIG. 1 shows the ratio of compound (I) in the total triglyceride of each triglyceride mixture obtained by a lipase exchange reaction for 1 hr and 4 hr in Example 4.

A triglyceride mixture after reaction for 4 hr was also subjected to the component analysis by high performance liquid chromatography in the same manner as above. Using the respective analysis results after reaction for 1 hr and after reaction for 4 hr, the peak area ratio of a peak having the same retention time as that of triglyceride containing HYA as one constituent fatty acid to all peaks was calculated and shown in FIG. 1. It was shown that the ratio (TG(H) %) of the aforementioned peak to the peak area increases by prolonging the reaction time, and formation of triglyceride containing HYA as one constituent fatty acid was found.

Then, the reaction product of triglyceride after reaction for 1 hr using respective edible fats and oils as the substrate was taken out by using TLC plate ("TLC Silica gel 60 F254": manufactured by Merck) for thin layer chromatography, subjected to saponification and methylation, and fatty acid composition was analyzed by gas chromatography ("GC-1700", manufactured by Shimadzu Corporation).

The fatty acid compositions before reaction of the respective fats and oils as the substrate are shown in Table 2, and the fatty acid compositions of the reaction products are shown in Table 3.

TABLE 1

| | State at standard temperature (about 20° C.) | Results of taste test | | | | | | |
|---|---|---|---|---|---|---|---|---|
| | | Five tastes | | | | | | total |
| | | umami taste | bitter taste | sour taste | saltiness | sweetness | acridity | oil odor | evaluation |
| Ex. 1 | liquid | 3.5 | 1 | 1 | 1.5 | 3.5 | 5 | 4 | 4 |
| Ex. 2 | liquid | 4 | 1 | 1 | 1 | 4 | 5 | 4.5 | 4 |
| Ex. 3 | liquid | 4 | 1 | 1 | 1 | 4 | 5 | 4.5 | 5 |
| Comp. Ex. 1 | liquid | 2.5 | 1 | 1 | 1 | 2 | 4 | 2 | 3 |
| Comp. Ex. 2 | solid | 1.5 | 3.5 | 1 | 1 | 1 | 1 | 3.5 | 1 |

The numerical values in Table 2 and Table 3 show the ratio (%) of each peak area of fatty acid detected by gas chromatography to the area of all peaks.

TABLE 2

Edible fats and oils (%)

| Constituent fatty acid | Linseed oil | Canola oil | Safflower oil | Soybean oil | Corn oil | Olive oil | Cottonseed oil | Coconut oil |
|---|---|---|---|---|---|---|---|---|
| lauric acid | | | | | | | | 48.1 |
| myristic acid | | | | | | | 0.5 | 20.4 |
| palmitic acid | 5.4 | 3.7 | 6.4 | 10.2 | 11.1 | 12.2 | 18.2 | 11.5 |
| stearic acid | 3.9 | 1.7 | 2.5 | 3.8 | 1.8 | 3.1 | 2.3 | 3.8 |
| oleic acid | 21 | 60.1 | 15.2 | 21 | 27.9 | 71.7 | 18.1 | 8.2 |
| linoleic acid | 15.3 | 18.8 | 72.6 | 53.4 | 54.4 | 8.2 | 56.7 | 2 |
| linolenic acid | 50.5 | 8.3 | 0.3 | 6.6 | 1.1 | 0.6 | 0.6 | 0.1 |
| others | 3.9 | 7.4 | 3 | 5 | 3.7 | 4.2 | 3.6 | 5.9 |

TABLE 3

Edible fats and oils (%)

| Constituent fatty acid | Linseed oil | Canola oil | Safflower oil | Soybean oil | Corn oil | Olive oil | Cottonseed oil | Coconut oil |
|---|---|---|---|---|---|---|---|---|
| lauric acid | 0 | 0 | 0 | 0 | 0 | 0 | 0 | 24 |
| myristic acid | 1.8 | 0.9 | 1 | 1.7 | 0.9 | 1.2 | 1.7 | 15 |
| palmitic acid | 13.4 | 10.6 | 15.8 | 19.6 | 14.1 | 15.7 | 20.1 | 13.4 |
| stearic acid | 5.3 | 4.2 | 5.7 | 7.5 | 4.6 | 6 | 5.9 | 4.9 |
| oleic acid | 22.3 | 36.3 | 18 | 21.2 | 22.7 | 31.9 | 19.5 | 8.7 |
| linoleic acid | 20.1 | 14.4 | 14.4 | 15.8 | 24.3 | 14.6 | 16.6 | 10.1 |
| linolenic acid | 5.3 | 0.7 | 0.6 | 0 | 0 | 0 | 0 | 0 |
| 10-hydroxy octadecanoic acid | 3 | 3 | 4.1 | 2.9 | 3.6 | 1.1 | 3.5 | 2.5 |
| HYA | 22.7 | 24.9 | 28.7 | 25.9 | 25.7 | 23.9 | 26.9 | 19.8 |
| others | 6.1 | 5 | 11.7 | 5.4 | 4.1 | 5.6 | 5.8 | 1.6 |

As shown in Table 2 and Table 3, the reaction product was confirmed to be a mixture of fats and oils containing compound (I) of the present invention since the constituent fatty acid contained HYA in all edible fats and oils used as the substrate. The results reveal that the acyl groups of compound (I) were derived from respective edible fats and oils except those derived from HYA.

From the above results, it was shown that compound (I) of the present invention can be produced by the above-mentioned production method 1 even when not only trilinolein used in Examples 1-3 but also triglyceride of edible fats and oils are used as the substrate.

[Example 5] Production of Compound (I) by Production Method 3

Figure 2:
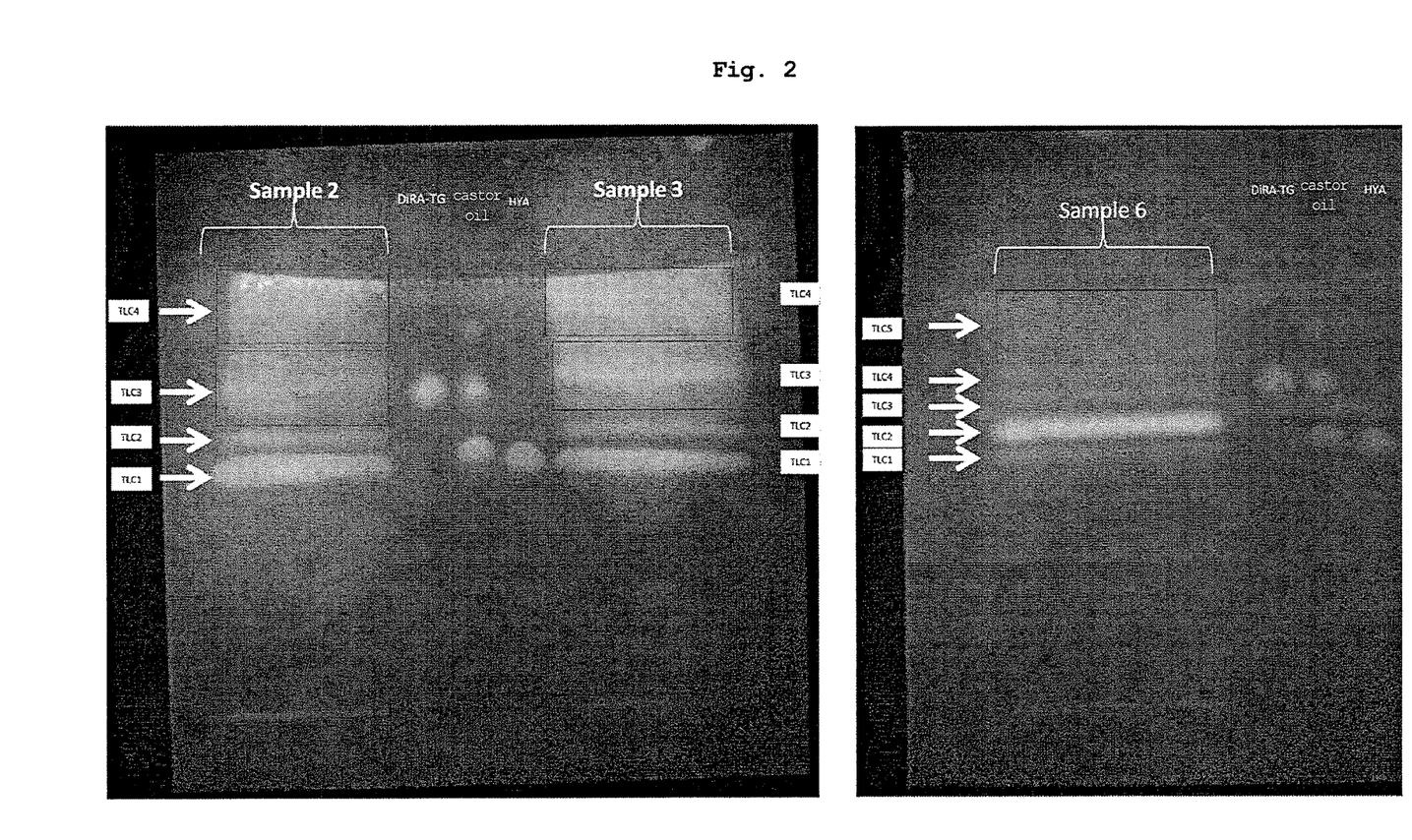
FIG. 2 shows TLC analysis results of the lipid extracted from each microorganism in Example 5.

In a 20 mL flask was placed GY medium (glucose 2%, yeast 1%) (4 mL), HYA was added to 10 mg/mL, respective microorganisms (*Basidiobolus ranarum*, *Basidiobolus haptosporus* and *Pleurotus ostreatus*) were each inoculated, and cultured at 28° C., stirring speed 120 rpm for 7 days. After culturing, the fungi were harvested by suction filtration with a nylon net filter (Filter Type: 30 μm, "NY30", manufactured by Merck Millipore), freeze-dried and pulverized with glass beads together with water, and the lipid was extracted by the Bligh-dyer method. The extracted lipid was separated by using TLC plate for thin layer chromatography ("TLC Silica gel 60 F254", manufactured by Merck) (hexane:diethyl ether:acetic acid=50 mL: 200 mL: 2.5 mL, Primulin color development, development for 40 min). Using a lipid sample extracted from *Basidiobolus ranarum* as Sample 2, a lipid sample extracted from *Basidiobolus haptosporus* as Sample 3, and a lipid sample extracted from *Pleurotus ostreatus* as Sample 6, the TLC analysis results thereof are shown in FIG. 2.

As the standard of TLC, castor oil having ricinoleic acid, which is a fatty acid having a hydroxyl group like HYA, as a constituent fatty acid of triglyceride, triglyceride having two ricinoleic acids purified from castor oil (DiRA-TG), and HYA, which is a free fatty acid, were used. The spots that can be confirmed in castor oil are the spots of triglyceride having three ricinoleic acids as the constituent fatty acid, triglyceride having two ricinoleic acids, and triglyceride having one ricinoleic acid (from the bottom). By a comparison of the positions of the spot of HYA, which is a free fatty acid, and the spots confirmed in castor oil, and those of the respective spots confirmed for Samples 2, 3, 6 (respective spots of TLC1-5 shown in FIG. 2), the respective spots of TLC2-TLC5 are considered to be the spots of triglyceride.

Respective spots (TLC1-5) were taken out from the TLC plate, subjected to saponification and methylation, and the fatty acid composition was analyzed by gas chromatography ("GC-1700", manufactured by Shimadzu Corporation). The analysis chart of the fatty acid composition of the lipid obtained from each microorganism is shown in FIG. 3. As shown in FIG. 3, it was found that HYA was contained as a constituent fatty acid in the triglyceride fraction of the lipid extracted from each microorganism. The results reveal that compound (I) can also be produced by production method 3.

INDUSTRIAL APPLICABILITY

It was found that compound (I) of the present invention is liquid at ambient temperature and has a good flavor, and permits easy ingestion and easy handling.

In addition, in the triglyceride or an optical isomer thereof of the present invention, the ester bond is hydrolyzed by lipase or the like in the body after ingestion to liberate HYA. Thus, superior physiological functions (lipid metabolism abnormality improving effect, action to increase intestinal immunity, intestinal inflammation suppressive action, etc.) as well as when HYA itself is ingested singly are expected to be exerted. Therefore, the triglyceride or an optical isomer thereof is industrially extremely useful in that it can be utilized as edible fat or oil utilizing the above-mentioned functions and can also be utilized as every kind of food or food additive and further, utilized in various fields such as pharmaceutical product, cosmetic, feed and the like.

This application is based on a patent application No. 2015-112604 filed in Japan, the contents of which are incorporated in full herein.

The invention claimed is:

1. A triglyceride in which at least one fatty acid forming an ester bond with a hydroxy group of glycerol is 10-hydroxy-cis-12-octadecenoic acid, or an optical isomer thereof.

2. The triglyceride or an optical isomer thereof according to claim 1, wherein two fatty acids forming an ester bond with a hydroxy group of glycerol are each 10-hydroxy-cis-12-octadecenoic acid.

3. The triglyceride or an optical isomer thereof according to claim 1, wherein three fatty acids forming an ester bond with a hydroxy group of glycerol are each 10-hydroxy-cis-12-octadecenoic acid.

4. The triglyceride or an optical isomer thereof according to claim 1, wherein a fatty acid other than 10-hydroxy-cis-12-octadecenoic acid in the fatty acids forming an ester bond with a hydroxy group of glycerol is a fatty acid having a carbon number of 8-22.

5. The triglyceride or an optical isomer thereof according to claim 4, wherein the fatty acid other than 10-hydroxy-cis-12-octadecenoic acid in the fatty acids forming an ester bond with a hydroxy group of glycerol is derived from an edible fat or oil.

6. The triglyceride or an optical isomer thereof according to claim 4, wherein the fatty acid other than 10-hydroxy-cis-12-octadecenoic acid in the fatty acids forming an ester bond with a hydroxy group of glycerol is one or more kinds selected from the group consisting of linoleic acid, α-linolenic acid, γ-linolenic acid, stearidonic acid, oleic acid, stearic acid, arachidonic acid, eicosapentaenoic acid, docosahexaenoic acid, caprylic acid, capric acid, lauric acid, myristic acid, palmitic acid, arachidic acid, pulmitoleic acid, elaidic acid, mead acid and dihomo-γ-linolenic acid.

7. The triglyceride or an optical isomer thereof according to claim 1, which is liquid at ambient temperature.

8. An edible fat or oil comprising the triglyceride or an optical isomer thereof according to claim 1.

9. A food or food additive comprising the triglyceride or an optical isomer thereof according to claim 1.

10. A pharmaceutical composition comprising the triglyceride or an optical isomer thereof according to claim 1.

11. An agent for the treatment of a disease selected from the group consisting of obesity, diabetes, lipid metabolism abnormality, hyperlipidemia, fatty liver, ulcerative colitis, Crohn's disease, ulcer, irritable bowel syndrome and inflammatory diseases, comprising the triglyceride or an optical isomer thereof according to claim 1.

12. A cosmetic or cosmetic additive comprising the triglyceride or an optical isomer thereof according to claim 1.

13. A feed or feed additive comprising the triglyceride or an optical isomer thereof according to claim 1.

14. The triglyceride or an optical isomer thereof according to claim 2, wherein a fatty acid other than 10-hydroxy-cis-12-octadecenoic acid in the fatty acids forming an ester bond with a hydroxy group of glycerol is a fatty acid having a carbon number of 8-22.

15. The triglyceride or an optical isomer thereof according to claim 14, wherein the fatty acid other than 10-hydroxy-cis-12-octadecenoic acid in the fatty acids forming an ester bond with a hydroxy group of glycerol is derived from an edible fat or oil.

16. The triglyceride or an optical isomer thereof according to claim 14, wherein the fatty acid other than 10-hydroxy-cis-12-octadecenoic acid in the fatty acids forming an ester bond with a hydroxy group of glycerol is one or more kinds selected from the group consisting of linoleic acid, α-linolenic acid, γ-linolenic acid, stearidonic acid, oleic acid, stearic acid, arachidonic acid, eicosapentaenoic acid, docosahexaenoic acid, caprylic acid, capric acid, lauric acid, myristic acid, palmitic acid, arachidic acid, pulmitoleic acid, elaidic acid, mead acid and dihomo-γ-linolenic acid.

17. The triglyceride or an optical isomer thereof according to claim 1, wherein one fatty acid forming an ester bond with a hydroxy group of glycerol is 10-hydroxy-cis-12-octadecenoic acid.

18. The triglyceride or an optical isomer thereof according to claim 17, wherein two fatty acids other than 10-hydroxy-cis-12-octadecenoic acid in the fatty acids forming an ester bond with a hydroxy group of glycerol are fatty acids having a carbon number of 8-22.

19. The triglyceride or an optical isomer thereof according to claim 17, wherein two fatty acids other than 10-hydroxy-cis-12-octadecenoic acid in the fatty acids forming an ester bond with a hydroxy group of glycerol are derived from an edible fat or oil.

20. The triglyceride or an optical isomer thereof according to claim 17, wherein two fatty acids other than 10-hydroxy-cis-12-octadecenoic acid in the fatty acids forming an ester bond with a hydroxy group of glycerol are one or more kinds selected from the group consisting of linoleic acid, α-linolenic acid, γ-linolenic acid, stearidonic acid, oleic acid, stearic acid, arachidonic acid, eicosapentaenoic acid, docosahexaenoic acid, caprylic acid, capric acid, lauric acid, myristic acid, palmitic acid, arachidic acid, pulmitoleic acid, elaidic acid, mead acid and dihomo-γ-linolenic acid.

21. The triglyceride or an optical isomer thereof according to claim 1, which is liquid at 20° C.

22. The triglyceride or an optical isomer thereof according to claim 2, which is liquid at 20° C.

23. The triglyceride or an optical isomer thereof according to claim 3, which is liquid at 20° C.

24. The triglyceride or an optical isomer thereof according to claim 17, which is liquid at 20° C.

* * * * *